United States Patent
Mower et al.

(10) Patent No.: US 9,566,446 B2
(45) Date of Patent: *Feb. 14, 2017

(54) SYSTEM AND METHOD FOR STIMULATING THE HEART VIA STORAGE OF MULTI-WAVEFORMS IN A CARDIAC STIMULATION DEVICE

(71) Applicant: MR3 Medical, LLC, North Oaks, MN (US)

(72) Inventors: Morton M. Mower, Denver, CO (US); Ralph Hall, North Oaks, MN (US)

(73) Assignee: MR3 MEDICAL, LLC, North Oaks, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/885,269

(22) Filed: Oct. 16, 2015

(65) Prior Publication Data
US 2016/0030742 A1    Feb. 4, 2016

Related U.S. Application Data

(63) Continuation of application No. 14/284,472, filed on May 22, 2014, now Pat. No. 9,186,516.

(60) Provisional application No. 61/826,071, filed on May 22, 2013.

(51) Int. Cl.
*A61N 1/362* (2006.01)
*A61N 1/368* (2006.01)

(52) U.S. Cl.
CPC ............ *A61N 1/368* (2013.01); *A61N 1/3628* (2013.01)

(58) Field of Classification Search
None
See application file for complete search history.

(56) References Cited

U.S. PATENT DOCUMENTS

| 5,871,506 | A | 2/1999 | Mower |
| 6,141,586 | A * | 10/2000 | Mower ............... A61N 1/3622 607/14 |
| 6,295,470 | B1 | 9/2001 | Mower |
| 9,186,516 | B2 * | 11/2015 | Mower ............... A61N 1/3628 |
| 9,220,904 | B2 * | 12/2015 | Mower ............... A61N 1/3628 |
| 2002/0188215 | A1 | 12/2002 | Ferek-Petric |
| 2008/0147138 | A1 | 6/2008 | Maskara et al. |
| 2008/0275520 | A1 | 11/2008 | Hopper et al. |
| 2009/0240298 | A1 | 9/2009 | Lian et al. |
| 2011/0071589 | A1 | 3/2011 | Starkebaum et al. |
| 2014/0350628 | A1 | 11/2014 | Mower |

* cited by examiner

*Primary Examiner* — Kennedy Schaetzle
(74) *Attorney, Agent, or Firm* — Oblon, McClelland, Maier & Neustadt, L.L.P.

(57) ABSTRACT

A rules engine acquires sensor data from sensors applied to the heart and determines whether an electrical waveform should be applied to the heart and, if so, the type of electrical waveform. A multi-phase cardiac stimulus generator generates waveforms in response to the rules engine from waveform data stored in a memory. The electrical waveform is applied to one or more electrodes implanted in or on the heart.

10 Claims, 2 Drawing Sheets

SYSTEM AND METHOD FOR STIMULATING THE HEART VIA STORAGE OF MULTI-WAVEFORMS IN A CARDIAC STIMULATION DEVICE

CROSS-REFERENCE TO RELATED APPLICATIONS

This application is a continuation of U.S. patent application Ser. No. 14/284,472 filed May 22, 2014, now U.S. Pat. No. 9,186,516, which claims the benefit of priority to U.S. Provisional Patent Application No. 61/826,071, entitled "System and Method for Stimulating the Heart via Storage of Multi-Waveforms in a Cardiac Stimulation Device" filed May 22, 2013. The entire contents of both of these applications are hereby incorporated by reference.

BACKGROUND

The heart is divided into the right side and the left side. The right side, comprising the right atrium and ventricle, collects and pumps de-oxygenated blood to the lungs to pick up oxygen. The left side, comprising the left atrium and ventricle, collects and pumps oxygenated blood to the body. Oxygen-poor blood returning from the body enters the right atrium through the vena cava. The right atrium contracts, pushing blood through the tricuspid valve and into the right ventricle. The right ventricle contracts to pump blood through the pulmonic valve and into the pulmonary artery, which connects to the lungs. The blood picks up oxygen in the lungs and then travels back to the heart through the pulmonary veins. The pulmonary veins empty into the left atrium, which contracts to push oxygenated blood into the left ventricle. The left ventricle contracts, pushing the blood through the aortic valve and into the aorta, which connects to the rest of the body. Coronary arteries extending from the aorta provide the heart blood.

The heart's own pacemaker is located in the atrium and is responsible for initiation of the heartbeat. The heartbeat begins with activation of atrial tissue in the pacemaker region (i.e., the sinoatrial (SA) node), followed by cell-to-cell spread of excitation throughout the atrium. The only normal link of excitable tissue connecting the atria to the ventricles is the atrioventricular (AV) node located at the boundary between the atria and the ventricles. Propagation takes place at a slow velocity, but at the ventricular end the bundle of His (i.e., the electrical conduction pathway located in the ventricular septum) and the bundle braides carry the excitation to many sites in the right and left ventricle at a relatively high velocity of 1-2 m/s. The slow conduction in the AV junction results in a delay of around 0.1 seconds between atrial and ventricular excitation. This timing facilitates terminal filling of the ventricles from atrial contraction prior to ventricular contraction. After the slowing of the AV node, the bundle of His separates into two bundle branches (left and right) propagating along each side of the septum. The bundles ramify into Purkinje fibers that diverge to the inner sides of the ventricular walls. This insures the propagation of excitatory waveforms within the ventricular conduction system proceeds at a relative high speed when compared to the propagation through the AV node.

When the heart is working properly, both of its lower chambers (ventricles) pump at the same time as, and in synchronization with, the pumping of the two upper chambers (atria). Up to 40 percent of heart failure patients, however, have disturbances in the conduction of electrical impulses to the ventricles (e.g., bundle branch block or intraventricular conduction delay). As a result, the left and right ventricles are activated at different times. When this happens, the walls of the left ventricle (the chamber responsible for pumping blood throughout the body) do not contract simultaneously, reducing the heart's efficiency as a pump. The heart typically responds by beating faster and dilating. This results in a vicious cycle of further dilation, constriction of the vessels in the body, salt and water retention, and further worsening of heart failure. These conduction delays do not respond to antiarrhythmics or other drugs.

Patients who have heart failure may be candidates to receive a pacemaker. A pacemaker is an artificial device to electrically assist in pacing the heart so that the heart may pump blood more effectively. Implantable electronic devices have been developed to treat both abnormally slow heart rates (bradycardias) and excessively rapid heart rates (tachycardias). The job of the pacemaker is to maintain a safe heart rate by delivering to the pumping chambers appropriately timed electrical impulses that replace the heart's normal rhythmic pulses. The device designed to perform this life-sustaining role consists of a power source the size of a silver dollar (containing the battery), and control circuits, wires or "leads" that connect the power source to the chambers of the heart. The leads are typically placed in contact with the right atrium or the right ventricle, or both. They allow the pacemaker to sense and stimulate in various combinations, depending on where the pacing is required.

Either cathodal or anodal current may be used to stimulate the myocardium. The pulses produced by most pacemakers are typically cathodal and excitatory. That is, the cathodal pulse is of sufficient magnitude and length to cause the heart to beat. Cathodal current comprises electrical pulses of negative polarity. This type of current depolarizes the cell membrane by discharging the membrane capacitor, and directly reduces the membrane potential toward threshold level. Cathodal current, by directly reducing the resting membrane potential toward threshold has a one-half to one-third lower threshold current in late diastole than does anodal current.

Modal current comprises electrical pulses of positive polarity. The effect of anodal current is to hyperpolarize the resting membrane. On sudden termination of the anodal pulse, the membrane potential returns towards resting level, overshoots to threshold, and a propagated response occurs. The use of anodal current to stimulate the myocardium is generally discouraged due to the higher stimulation threshold, which leads to use of a higher current, resulting in a drain on the battery of an implanted device and impaired longevity. Additionally, the use of anodal current for cardiac stimulation was discouraged due to the suspicion that the anodal contribution to depolarization can, particularly at higher voltages, contribute to arrhythmogenesis.

It has been shown that pacing in which a combination of cathodal and anodal pulses of either a stimulating or conditioning nature preserves the improved conduction and contractility of anodal pacing while eliminating the drawback of increased stimulation threshold. The result is a depolarization wave of increased speed. This increased propagation speed results in superior cardiac contraction leading to an improvement in blood flow. Improved stimulation at a lower voltage level also results in reduction in power consumption and increased life for pacemaker batteries.

SUMMARY

In an embodiment, a memory is configured to store one or more anodal waveforms, cathodal waveforms, and biphasic waveforms. A waveform or a combination of waveforms may be selected from the memory by a processor based on sensor data, data about the user and rules also stored in the memory. The stored waveforms comprise waveform data that are used by a multi-phase cardiac stimulus generator to produce waveforms for applying to the heart.

In an embodiment, different pacing waveforms are generated by the multi-phase cardiac stimulus generator to differentially increase or decrease conduction, vigor of conduction, and repolarization in various directions, amounts, and combinations.

In another embodiment, various non-stimulatory waveforms of different polarities, combinations, and timings may be selectively generated by the multi-phase cardiac stimulus to affect ion channels involved in repolarization.

DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

As used herein, the term "pulse" refers to a single occurrence of an electrical signal that has a defined shaped and period.

As used herein, the term "waveform" refers to a repeating electrical signal that may include one or more pulses. The pulses that make up the waveform may be the same or may differ in any one of shape, polarity, duration and amplitude. For example, a biphasic waveform may include an anodal pulse and a cathodal pulse. The anodal and cathodal components may differ only in polarity or may differ in shape, polarity, duration and amplitude. Pulses making up a waveform may differ in shape, polarity, duration, and amplitude but be equivalent in power.

As used herein, the term "sub-threshold waveform" refers to a waveform that does not result in stimulating the heart to beat. A waveform may be sub-threshold because the amplitude of the waveform is below an amplitude threshold value necessary to stimulate a heartbeat. A waveform may be sub-threshold because the duration of the waveform is below a duration threshold value necessary to stimulate a heartbeat. A waveform may be sub-threshold because the power of the waveform is below a power threshold value necessary to stimulate a heartbeat.

As used herein, the term "pacing waveform" refers to a waveform that stimulates a heartbeat, results in depolarization and is by definition equal to or greater than a threshold necessary to simulate a heartbeat.

Figure 1:
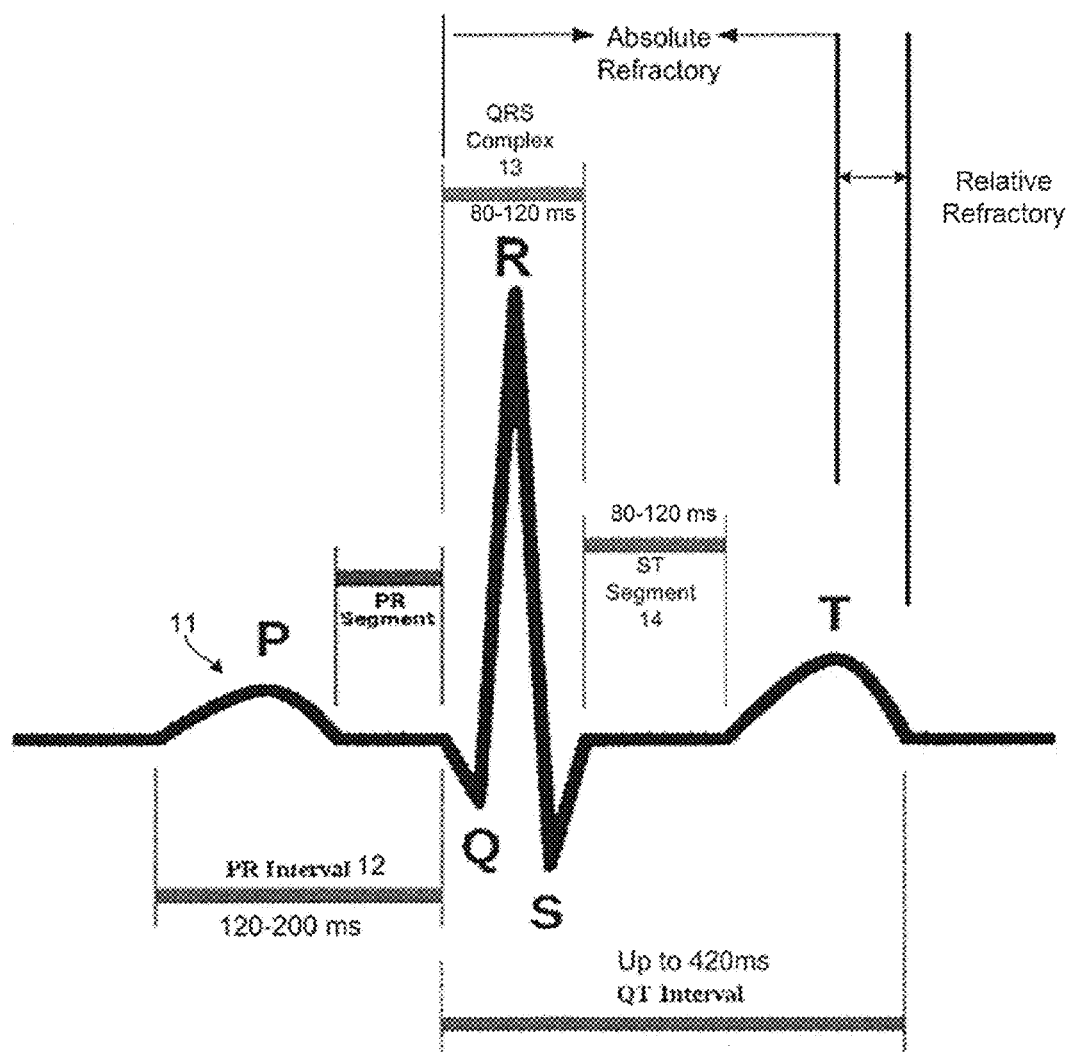
FIG. 1 is a schematic representation of the electrical activity of a typical heartbeat as is known in the prior art.

FIG. 1 shows a representative tracing 10 of electrical activity in a typical heartbeat. A P wave 11 represents the wave of depolarization that spreads from the SA node throughout the atria. A period of time from the onset of the P wave to the beginning of a QRS complex is known as the P-R interval 12. The P-R interval 12 represents the time between the onset of atrial depolarization and the onset of ventricular depolarization (typically lasting 20-200 ms). If the P-R interval is >200 ms, there is an AV conduction block, which is also known as a first-degree heart block if the impulse is still able to be conducted into the ventricles.

A QRS complex 13 represents the period of ventricular depolarization, which normally occurs very rapidly (e.g., typically lasting 80-120 ms). If the QRS complex is prolonged, conduction is impaired within the ventricles.

The isoelectric period (ST segment 14) following the QRS complex 13 is the period of time (typically lasting 80-120 ms) at which the entire ventricle is depolarized and roughly corresponds to the plateau phase of the ventricular action potential. The ST segment 14 is important in the diagnosis of ventricular ischemia or hypoxia because under those conditions, the ST segment 14 can become either depressed or elevated.

Figure 2:
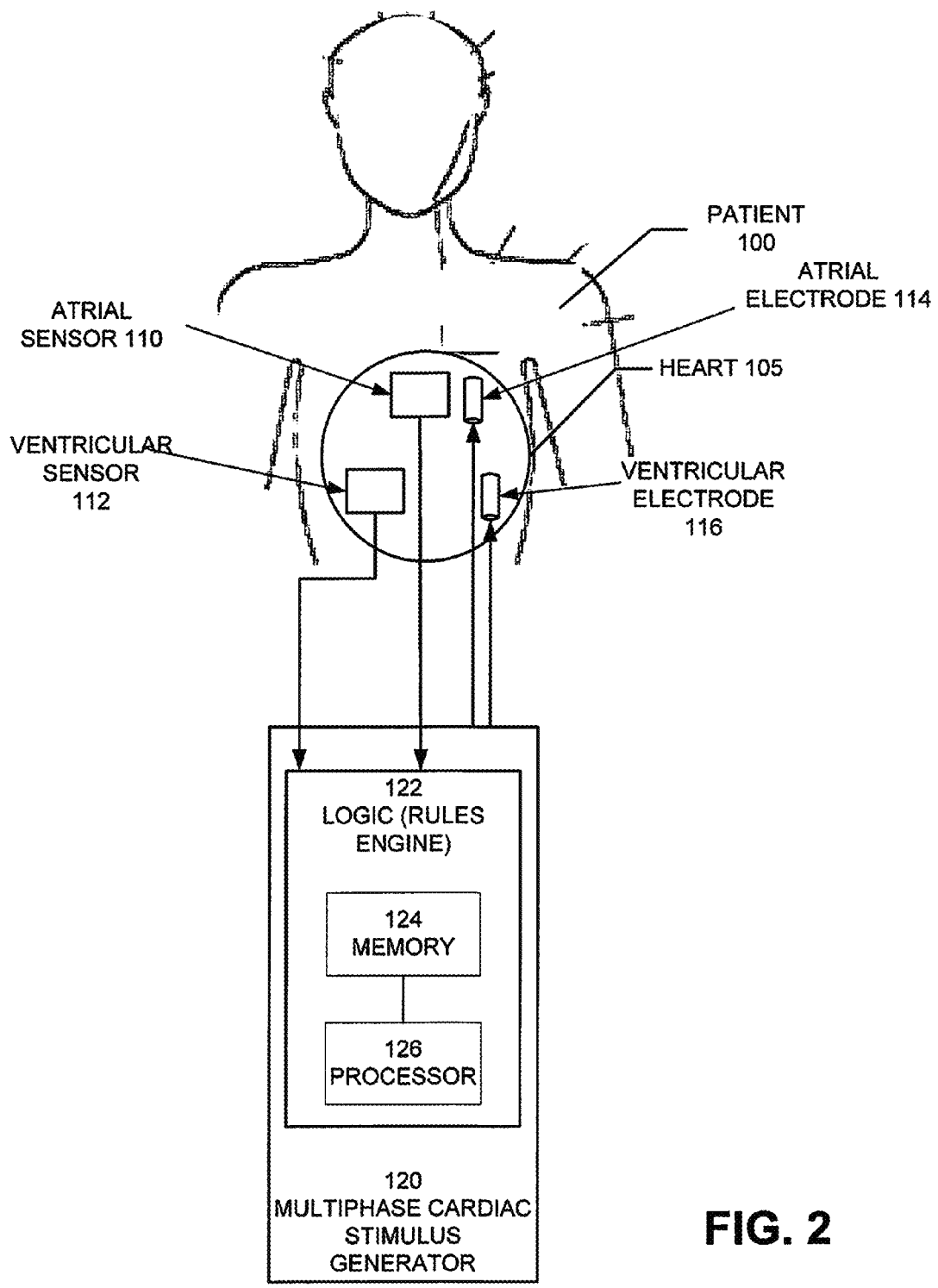
FIG. 2 is a schematic representation illustrating a cardiac stimulation device according to an embodiment.

FIG. 2 is a schematic representation illustrating a multi-phase cardiac stimulus generator 120 implanted in a patient according to an embodiment. In an embodiment, one or more sensors sense rhythm and contractions of the patient's heart 105 using at least one of atrial sensing and ventricular sensing, such as at least one of atrial sensor 110 and ventricular sensor 112. The atrial sensor 110 and/or ventricular sensor 112 provide sensor data to a rules engine 122. In an embodiment, the rules engine includes a processor 126 and a memory 124 for storing rules and receiving sensor data. The rules engine 122 may poll the one or more of the atrial sensor 110 and the ventricular sensor 112 to obtain sensor data and to apply the rules to the sensor data in order to determine whether to deliver electrical waveforms to one or more electrodes, and, if electrical waveforms are to be delivered, which of the one or more electrodes is to receive the electrical waveforms. In an embodiment, the one or more electrodes may be an atrial electrode 114 and a ventricular electrode 116, and may provide electrical waveforms to at least one of an atrial chamber and a ventricular chamber of the heart 105. The multi-phase cardiac stimulus generator 120 may generate an anodal waveform, a cathodal waveform, and a biphasic waveform above or below threshold depending on the sensor data and the rules applied by the rules engine 122.

In an embodiment, the memory 124 of the rules engine 122 of the multi-phase cardiac stimulus generator 120 is configured to store one or more anodal waveforms, cathodal waveforms, and biphasic waveforms. A waveform or a combination of waveforms may be selected from the memory 124 by the processor 126 based on sensor data and based on rules also stored in memory 124.

In an embodiment, the memory 124 also stores information about the patient 100. The processor 126 may further select a waveform or a combination of waveforms from the stored waveforms based on the sensor data and data about the user.

In an embodiment, the stored waveforms comprise waveform data that are used by the multi-phase cardiac stimulus generator 120 to produce waveforms for applying to the heart 105.

In an embodiment, different pacing waveforms are generated by the multi-phase cardiac stimulus generator 120 to differentially increase or decrease conduction, vigor of conduction, and repolarization in various directions, amounts, and combinations. For example, a patient with Idiopathic Hypertrophic Subaortic Stenosis (IHSS) may experience vigorous contraction of the IV septum, which leads to LV outflow tract obstruction. This condition can be relieved by pacing the septum with a monophasic cathodal waveform. A patient with congestive heart failure (CHF) can be improved by speeding conduction and resynchronizing the heart muscle by reducing the QRS width by generating and applying biphasic pacing waveforms.

In another embodiment, various non-stimulatory waveforms of different polarities, combinations, and timings may be selectively generated by the multi-phase cardiac stimulus generator 120 to affect ion channels involved in repolarization specifically and selectively. For example, a waveform may be generated by the multi-phase cardiac stimulus generator 120 to normalize abnormalities resulting from genetic disorders and various medications. In an embodiment, the total duration of these waveforms can also be optimized to promote stimulation of nervous tissue, myocardium, or skeletal muscle.

In an embodiment, the one or more atrial sensor 110 and/or ventricular sensor 112 may include sensors that measure various measures of heart activity and health. By way of illustration and not by way of limitation, sensors may be used to measure heart size, asynchronicity of contractions, back pressures in various parts of the heart, intrinsic QRS width, resting membrane potential (RMP), and after potentials of the action potential. By way of illustration and not by way of limitation, measurements may be taken using intra-cellular plunge electrodes, monophasic action potential (MAP) catheters, and optical probes. The sensor data may be used to diagnose various abnormal conditions and/or to generate waveforms to treat one or more conditions.

In an alternative embodiment, only a limited number of waveforms are stored in the memory 124 of the rules engine 122 of the multi-phase cardiac stimulus generator 120. The stored waveforms may be selected based on the condition of the patient and the anticipated abnormal states that the patient may encounter.

The stored waveforms may be differentiated based on a strength and a duration of an anodal portion of the biphasic waveform. The stored waveforms may also be differentiated based on a strength and a duration of a cathodal portion of the biphasic waveform.

For example, a shorter waveform may be used to enhance conduction without stimulating the heart. This will allow intrinsic conduction to be normalized.

In an embodiment, the sensor data in conjunction with the user data may follow a non-stimulatory short waveform with a stimulatory biphasic or cathodal pacing waveform. Alternatively, a longer waveform may be used to enhance contractility.

In an embodiment, the selection of a biphasic waveform and/or a cathodal waveform may be based on sensor data. For example, sensor data may be acquired from atrial sensor 110, ventricular sensor 112, or other sensors. For example, the sensor data may be acquired from the atrial sensor 110 and a septum sensor (not illustrated) to evaluate the condition of the patient. An appropriate waveform may be selected the processor 126.

A patient may have different heart conditions simultaneously. The sensor data may be used to select an appropriate waveform from memory 124 and to provide the appropriate waveform data to the multi-phase cardiac stimulus generator 120. The selected waveform is then applied to the heart, and the heart rhythm is sensed. The new sensing data may be used to again apply the waveform to the heart, to modify the strength of the applied waveform and to apply the modified waveform to the heart, to apply a different waveform to the heart, or to cease stimulating the heart.

A system and method for stimulating the heart via storage of multi-waveforms in a cardiac stimulation device t have been disclosed. It will also be understood that the invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the" is not to be construed as limiting the element to the singular.

What is claimed is:

1. An apparatus for providing electrical therapy to a heart, comprising:
   circuitry configured to:
      store a plurality of waveforms and a plurality of rules;
      apply at least one of the plurality of rules to sensor data received from sensors that sense parameters of the heart;
      determine whether to deliver an electrical waveform to the heart based on the application of the at least one of the plurality of rules to the sensor data; and
      when it is determined that the electrical waveform is to be delivered to the heart:
         select one of the plurality of waveforms based on the application of the at least one of the plurality of rules to the sensor data,
         cause a waveform generator to generate an output waveform based on the selected one of the plurality of waveforms, and
         deliver the output waveform to the heart via at least one electrode and at a timing based on the application of the at least one of the plurality of rules to the sensor data.

2. The apparatus according to claim 1, wherein the selected one of the plurality of waveforms is a biphasic waveform.

3. The apparatus according to claim 1, wherein the selected one of the plurality of waveforms is a sub-threshold waveform.

4. The apparatus according to claim 1, wherein the plurality of waveforms include a sub-threshold anodal pulse, an excitatory anodal pulse, a sub-threshold cathodal pulse, and an excitatory cathodal pulse.

5. The apparatus according to claim 1, wherein the circuitry is further configured to store patient data and to select the one of the plurality of waveforms based on application of the rules to the sensor data and the patient data.

6. A method for providing electrical therapy to a heart, comprising:
   storing, with circuitry, a plurality of waveforms and a plurality of rules;
   applying, with the circuitry, at least one of the plurality of rules to sensor data received from sensors that sense parameters of the heart;
   determining, with the circuitry, whether to deliver an electrical waveform to the heart based on the application of the at least one of the plurality of rules to the sensor data; and
   when it is determined that the electrical waveform is to be delivered to the heart:
      selecting, with the circuitry, one of the plurality of waveforms based on the application of the at least one of the plurality of rules to the sensor data,
      causing, with the circuitry, a waveform generator to generate an output waveform based on the selected one of the plurality of waveforms, and
      delivering, with the circuitry, the output waveform to the heart via at least one electrode and at a timing based on the application of the at least one of the plurality of rules to the sensor data.

7. The method according to claim 6, wherein the selected one of the plurality of waveforms is a biphasic waveform.

8. The method according to claim 6, wherein the selected one of the plurality of waveforms is a sub-threshold waveform.

9. The method according to claim 6, wherein the plurality of waveforms include a sub-threshold anodal pulse, an excitatory anodal pulse, a sub-threshold cathodal pulse, and an excitatory cathodal pulse.

10. The method according to claim 6, further comprising:
storing, with the circuitry, patient data; and
selecting, with the circuitry, the one of the plurality of waveforms based on application of the rules to the sensor data and the patient data.

* * * * *